(12) United States Patent
Heinz et al.

(10) Patent No.: US 9,828,577 B2
(45) Date of Patent: Nov. 28, 2017

(54) SYSTEM AND METHOD TO MONITOR VISCOSITY CHANGES OF A FLUID STORED IN A VOLUME

(71) Applicant: GENERAL ELECTRIC COMPANY, Schenectady, NY (US)

(72) Inventors: Gregory Heinz, Mukwonago, WI (US); Jimmie Beacham, Jr., West Allis, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 37 days.

(21) Appl. No.: 14/985,074

(22) Filed: Dec. 30, 2015

(65) Prior Publication Data

US 2017/0191017 A1   Jul. 6, 2017

(51) Int. Cl.
| | |
|---|---|
| *C12Q 1/00* | (2006.01) |
| *C12M 3/06* | (2006.01) |
| *C12M 1/36* | (2006.01) |
| *C12M 1/00* | (2006.01) |
| *C12Q 3/00* | (2006.01) |

(52) U.S. Cl.
CPC ............ *C12M 27/16* (2013.01); *C12M 23/26* (2013.01); *C12M 41/48* (2013.01); *C12Q 3/00* (2013.01)

(58) Field of Classification Search
None
See application file for complete search history.

(56) References Cited

U.S. PATENT DOCUMENTS

| | | | | |
|---|---|---|---|---|
| 6,544,788 | B2 * | 4/2003 | Singh | .................. B01F 11/0017 435/297.1 |
| 2009/0104594 | A1 * | 4/2009 | Webb | ..................... C12M 41/48 435/3 |
| 2013/0323841 | A1 * | 12/2013 | Kruglick | ................ C12M 25/00 435/402 |
| 2015/0300873 | A1 * | 10/2015 | Kjar | ....................... G01G 17/00 73/862.382 |

* cited by examiner

*Primary Examiner* — Chris L Chin

(57) ABSTRACT

A system and method for monitoring viscosity changes of a fluid stored in a volume are provided. The system includes a flexible chamber configured to receive and hold the fluid, a motion generator configured to induce a wave motion within the fluid, at least one sensor affixed at least in part to a portion of the flexible chamber and configured to measure at least a strain on a portion of the flexible chamber and generate an associated strain output. The strain output is effectuated by the wave motion of the fluid within the flexible chamber and correlates to a viscosity value of the fluid. A computer or controller is configured to receive the strain output from the sensor at a given time, compare the viscosity value associated with the strain output to a reference viscosity value, and determine whether to adjust the wave motion generated by the motion generator.

20 Claims, 4 Drawing Sheets

SYSTEM AND METHOD TO MONITOR VISCOSITY CHANGES OF A FLUID STORED IN A VOLUME

BACKGROUND

Single-use bioreactor systems are commonly used for cell culture applications. The growth and culture of mammalian cells, for instance, typically require a constant supply of adequate oxygen. Oxygen diffusion in culture media is a function of a liquid-to-air surface area when operating the bioreactor. Furthermore, oxygen transfer is limited by the liquid-to-air surface area and any shear forces created by agitation and/or sparging.

Both bubbling and agitation typically have a detrimental effect on biological cells, such as mammalian cell cultures. Biological cells may be rendered non-viable through bubble breakup and/or coalescence within the culture media, especially at a surface gas-to-liquid interface. Therefore, maximizing oxygen transfer in the bioreactor must be balanced by maintaining cell viability.

A rocking motion of the bioreactor promotes wave formation in the bag which provides liquid mixing and enhances oxygen transfer. Additionally, the bioreactor provides an excellent environment for cell growth and expression due to the low shear generated by the gentle wave agitation and bubble-free aeration system.

SUMMARY

In accordance with an embodiment of the present invention, there is provided a system for monitoring viscosity changes of a fluid stored in a volume. The system comprises a flexible chamber, a motion generator, at least one sensor, and a computer or controller. The flexible chamber defines the volume and is configured to receive and hold the fluid. The motion generator is configured to induce a wave motion within the fluid. The at least one sensor is affixed at least in part to a portion of the flexible chamber and is configured to measure at least a strain on a portion of the flexible chamber and generate an associated strain output. The strain output is effectuated by the wave motion of the fluid within the flexible chamber, wherein the strain output correlates to a viscosity value of the fluid. The computer or controller is configured to receive the strain output from the sensor at a given time, compare the viscosity value associated with the strain output to a reference viscosity value, and determine, based on the comparison, whether to adjust the wave motion generated by the motion generator.

In accordance with another embodiment of the present invention, there is provided a method for monitoring viscosity changes of a fluid stored in a volume. The method comprises receiving strain output from a sensor at a given time, comparing the viscosity value associated with the strain output to a reference viscosity value, and determining, based on the comparison, whether to adjust the wave motion generated by the motion generator.

In accordance with another embodiment of the present invention, there is provided a method for manufacturing a flexible chamber to be used in a system for monitoring viscosity changes of a fluid stored in a volume. The method comprises providing a first piece of plastic film, creating one or more holes into the first piece of plastic film to form at least one port aperture, and welding or otherwise attaching a port apparatus to the flexible chamber at the at least one port aperture. Further, the method comprises attaching the first piece of plastic film to a second piece of plastic film by sealing at least one edge, and 3D printing one or more sensors comprising stretchable elastomer circuit traces onto a surface of the flexible chamber.

In addition to the aspects and advantages described in this summary, further aspects and advantages will become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
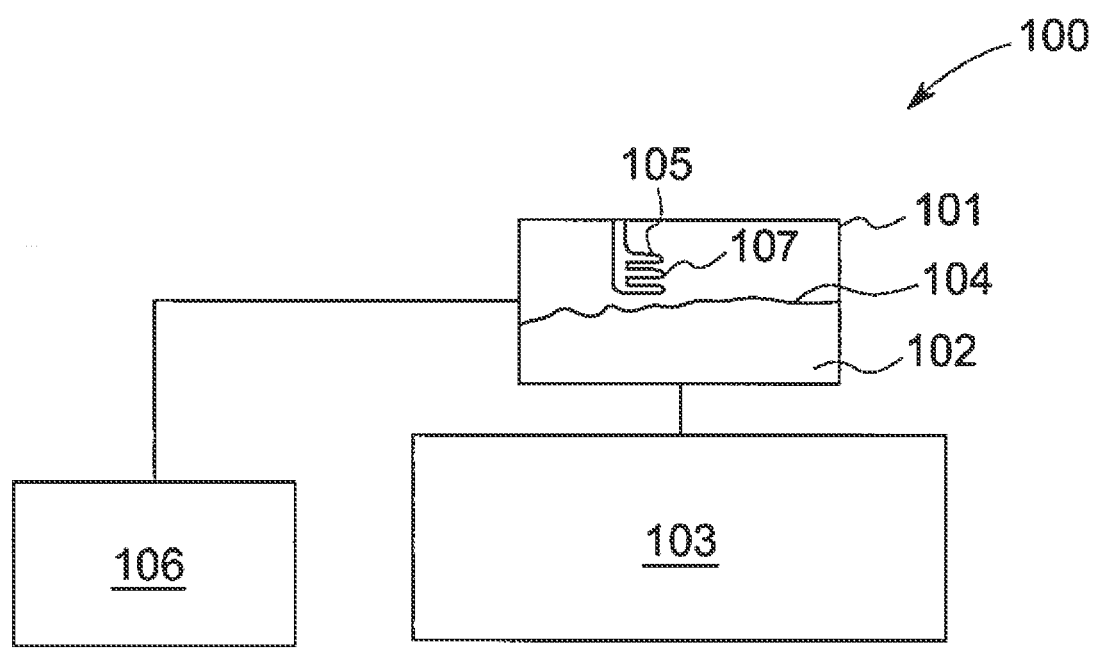
FIG. 1 shows a schematic diagram of the system for monitoring viscosity changes of a fluid stored in a volume as described herein.

FIG. 1 shows one embodiment of a system 100 for monitoring viscosity changes of a fluid 102 stored in a volume. Said fluid can be a liquid, a gas, a plasma, a flowing material or substance, or any combination thereof. In at least one embodiment, said fluid comprises one or more types of living or active cells, viruses, prions, self-replicating molecules, or any combination thereof, in a culture media which may include one or more supporting materials to encourage growth and proliferation such as, for example, oxygen and nutrients.

The system 100 generally comprises a flexible chamber or volume 101, a motion generator 103, at least one sensor 105, and a computer or controller 106. The flexible chamber 101 defines a volume and is configured to receive and hold a fluid 102. The motion generator 103 is configured to induce a wave motion 104 within the fluid 102.

FIG. 1 also shows at least one sensor 105 affixed at least in part to a portion of the flexible chamber 101. The at least one sensor 105 is configured to measure at least a strain on a portion of the flexible chamber 101 and generate an associated strain output. The strain output is effectuated by the wave motion 104 of the fluid 102 within the flexible chamber 101. In this embodiment the strain output also correlates to a viscosity value of the fluid 102. One having ordinary skill in the art would appreciate that the sensor 105 could be a strain gauge 205, a device that is very well understood. One having ordinary skill in the art would also appreciate that the sensor could be a multi-sensor that in addition to measuring strain could also measure pH or temperature, for example, simultaneously with the same device. Sensors have long been used in conjunction with rocking cell bag bioreactors to measure various aspects of cell culture, including dissolved-oxygen, temperature, and pH. Presently, there are no systems or methods for measuring or monitoring waveform to optimize cell mixture and transfer of oxygen. Data received from measuring viscosity changes of a fluid stored in a volume by way of strain output received from a stain sensor can provide information regarding the waveform to improve cell culture analysis and process optimization.

Electrical conductivity of the sensor 105 or strain gauge 205 associated with the flexible chamber 101 will fluctuate as the geometry of the flexible chamber 101 changes. When the flexible chamber 101 is moved by the motion generator 103, a wave 104 or series of waves are generated within the fluid 102 inside the flexible chamber 101 and will continuously reshape the flexible chamber 101, causing a deformation of an electrical conducting element 107 within the sensor 105. As the conducting element 107 deforms its electrical resistance will change; for example, a stretching of the element may increase its resistance, while a compressing of the element may decrease its resistance, or vice versa. Accordingly, the sensor 105 will output a signal corresponding to the changes in electrical resistance and will allow for the determination of strain to be used to account for viscosity changes in the fluid 102 over time as the flexible chamber 101 deforms in accordance with the wave motion 104. The sensor 105 may be one of many types of known strain gauges; for example, the sensor 105 may be, but is not limited to, one of a piezoresistor, or an electrical, mechanical, or electromechanical strain gauge.

The system 102 further comprises a computer or controller 106. The computer or controller 106 is configured to receive the strain outputs from the sensor 105 at a given time or over a period of time. The given time may be a set interval of time. For example, the set interval may be every minute or every hour, depending on the particularity of the fluid or cell culture inside the flexible chamber 101. The computer or controller 106 will compare the viscosity value associated with the strain output received from the sensor at a given time to a reference viscosity value. The reference viscosity value is derived from a predetermined database of values which, in at least one embodiment, corresponds to or is directly linked to the type of the cell(s) or cell culture(s) residing inside the flexible chamber 101. In at least one embodiment, the cell culture comprises one or more distinct cell types in addition to any supporting materials, such as nutrients, needed to develop, grow and/or proliferate the cells. The reference viscosity value may be an earlier measurement of strain output received from the sensor 105 or an estimated optimal value based on previous or known data. Continuous measurement of strain correlating to the wave motion of the fluid 102 within the flexible chamber 101 will provide continuous feedback control and allow for optimization.

Figure 2A:
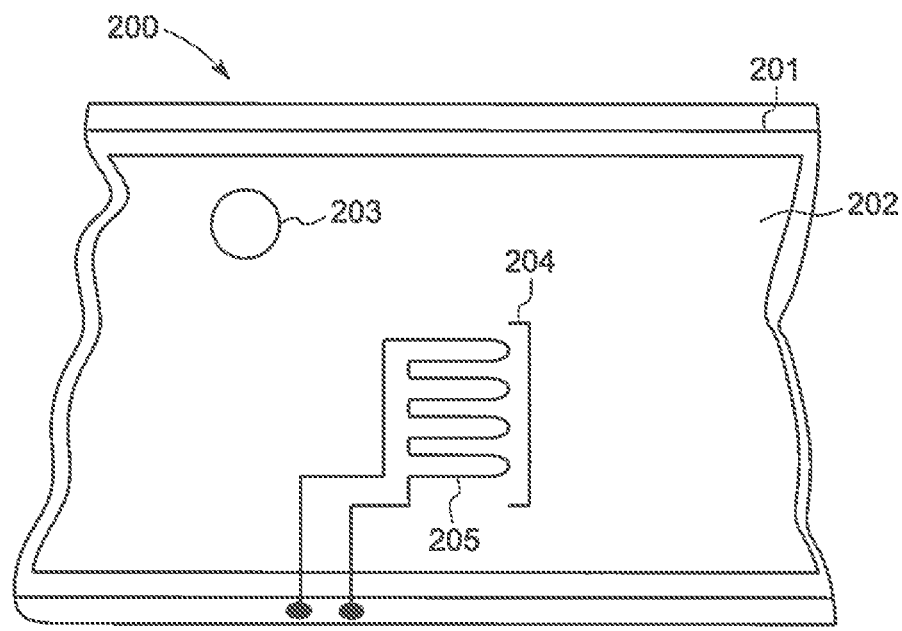
FIG. 2a shows a top view of a detailed schematic diagram of the flexible container with at least one sensor as described herein.
Figure 2B:
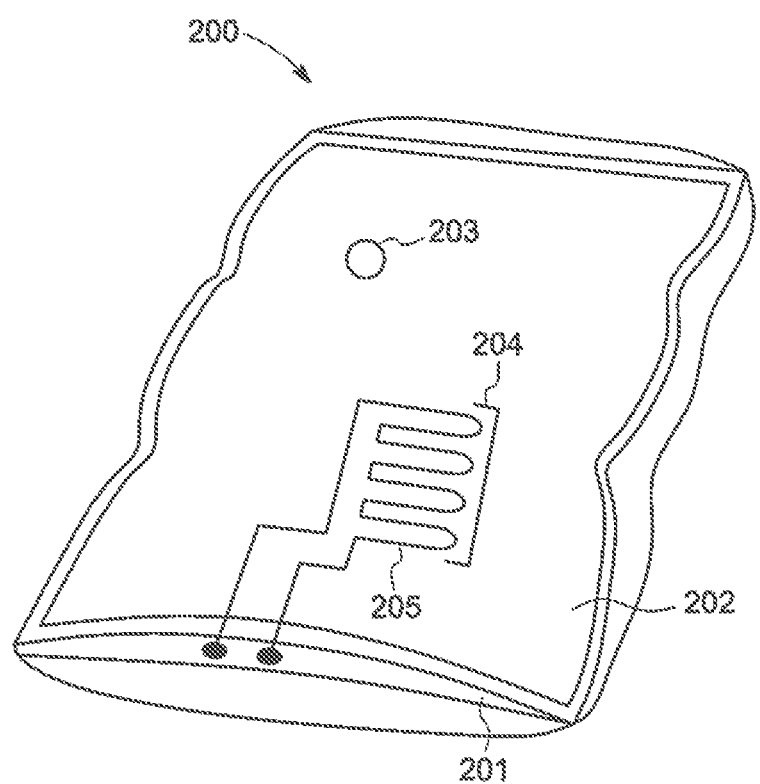
FIG. 2b shows an isometric view of a detailed schematic diagram of the flexible container with at least one sensor as described herein.

FIGS. 2a and 2b show a detailed schematic diagram of one embodiment of the flexible chamber, wherein said embodiment is a cell bag bioreactor 200. FIG. 2a shows a top view of a cell bag bioreactor with at least one sensor as described herein while FIG. 2b shows an isometric view of the same cell bag bioreactor with at least one sensor as described herein. The cell bag bioreactor 200 in this embodiment has at least one sealed edge 201 and a surface 202.

Also, there is present at least one port 203 on the surface 202 through which cell culture media and any supporting materials can be introduced or removed as needed. One having skill in the art would appreciate that multiple ports could be added at any desired location on the cell bag bioreactor 200 depending, for example, on the needs of a particular cell culture protocol and/or on the layout/location/type of equipment used in conjunction with the cell bag bioreactor 200.

In this embodiment the sensor is a strain gauge 204, such as the strain gauge described above, comprising a flexible conductive member 205, such as a stretchable and/or compressible conductive metal, elastomer or combinations thereof, which may be affixed or adhered to a surface of the cell bag bioreactor or printed directly on the surface of the cell bag bioreactor using, for example, a 3D printing process. The flexible conductive member 205 flexes (e.g. stretches and/or compresses) as the a surface of the cell bag bioreactor 200 flexes and accurately measures strain on the bag surface as it reacts to the wave motion of the fluid within the bag, said strain effectuated by the wave motion and, as is well known, is a function of the changing electrical resistance of the conductive member 205 as it flexes.

Figure 3:
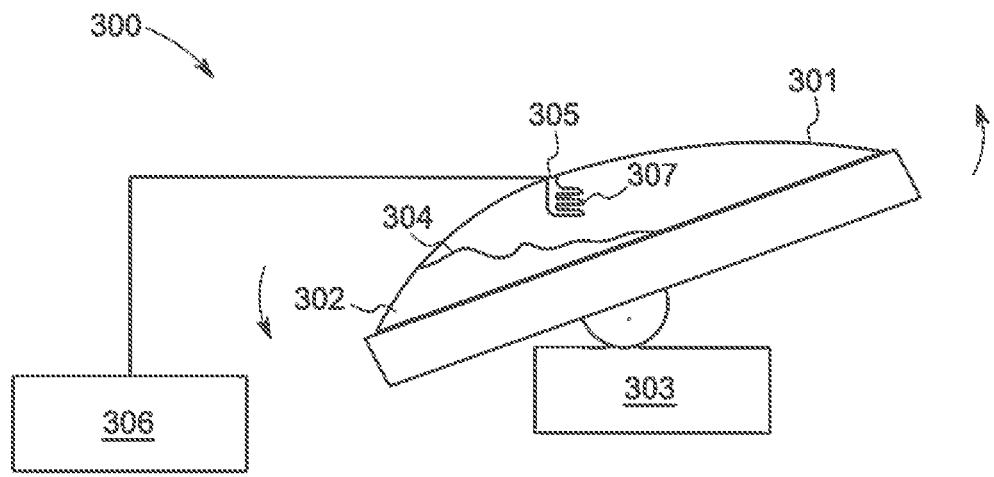
FIG. 3 shows the system for monitoring viscosity changes of a fluid stored in a volume according to one embodiment.

FIG. 3 depicts a system 300 for monitoring viscosity changes of a fluid stored in a flexible chamber according to another embodiment. In this embodiment, the flexible chamber of the system 300 is a cell bag bioreactor 301 and the at least one sensor 305 is a strain gauge. In one embodiment said strain gauge is made comprising 3D printed flexible (e.g. stretchable and/or compressible) conductive material 307, such as an elastomer, metal or combinations thereof. The flexible conductive material 307 allows the sensor to flex (e.g. stretch and/or compress) as the cell bag bioreactor flexes and, as explained above, to accurately measure the strain on the bag surface as it reacts to the wave motion of the fluid within the bag. Also in this embodiment, the motion generator is a rocking platform 303. The rocking platform 303 is configured to have one or multiple degrees of freedom to induce a wave motion 304 within the fluid 302 inside the cell bag bioreactor 301; said fluid, for example, comprising one or more distinct biological cell types with or without supporting materials, such as nutrients, needed to develop, grow and/or proliferate the cells. In at least one embodiment, the fluid is a cell culture or batch culture comprising any combination of biological cells and cell culture media to promote and sustain cell growth.

The system 300 also comprises a computer, processor, and/or controller 306. The computer, processor, and/or controller 306 is configured to receive the strain output from the sensor 305 at a given time determined by the user. The given time may be a set interval of time. For example, the set interval may be every minute or every hour, depending on the particularity of the cell culture. The computer, processor, or controller 306 is configured to compare the viscosity value associated with the strain output received from the sensor to a reference viscosity value. The reference viscosity value is derived from a predetermined database of values. As noted above, the reference viscosity value may be an earlier measurement of strain output received from the sensor 305 or an estimated optimal value based on previous or known data. Continuous measurement of strain correlating to the wave motion of the cell culture 302 within the cell bag bioreactor 301 will provide continuous feedback control and allow for optimization of the growth of the cell culture 302.

Figure 4:
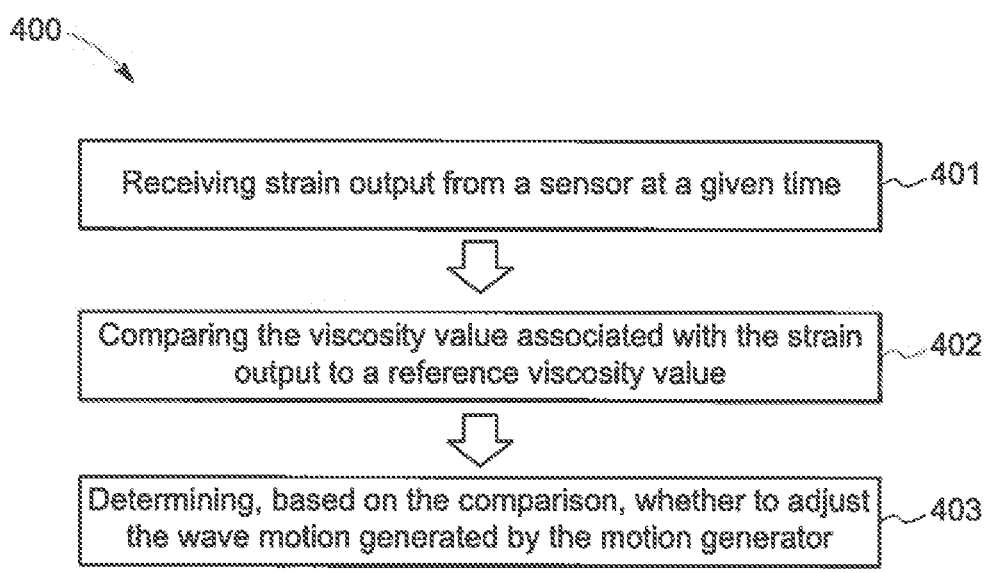
FIG. 4 shows a flow diagram of an embodiment of monitoring viscosity changes of a fluid stored in a volume as described herein.

FIG. 4 shows a flow diagram of one embodiment of a method for monitoring viscosity changes 400 of a fluid stored in a flexible chamber with at least one sensor affixed thereto to form, for example, a cell bag bioreactor. As mentioned above, the sensor may be a strain gauge, of which there are many types. The sensor 105 may be, but is not limited to, one of a piezoresistor, an electrical, mechanical, electromechanical strain gauge, optical sensor, or any sensor, combination of sensors and/or devices configured to measure the viscosity of a fluid or provide data usable in determining the viscosity of a fluid. The method commences at step 401 wherein a strain output is received from a sensor at a given time. Next, there is assigned a viscosity value associated with the strain output. The assigned viscosity value is compared to a reference viscosity value 402, and based upon the comparison of the assigned viscosity value and the reference viscosity value, a determination is made as to whether or not to adjust the wave motion generated by the motion generator; and if an adjustment is to be made, to what degree or extent one or more wave parameters is adjusted—for example, to what level should the frequency, amplitude and/or velocity (e.g. phase velocity and/or group velocity) of the generated waves be increased or decreased.

Figure 5:
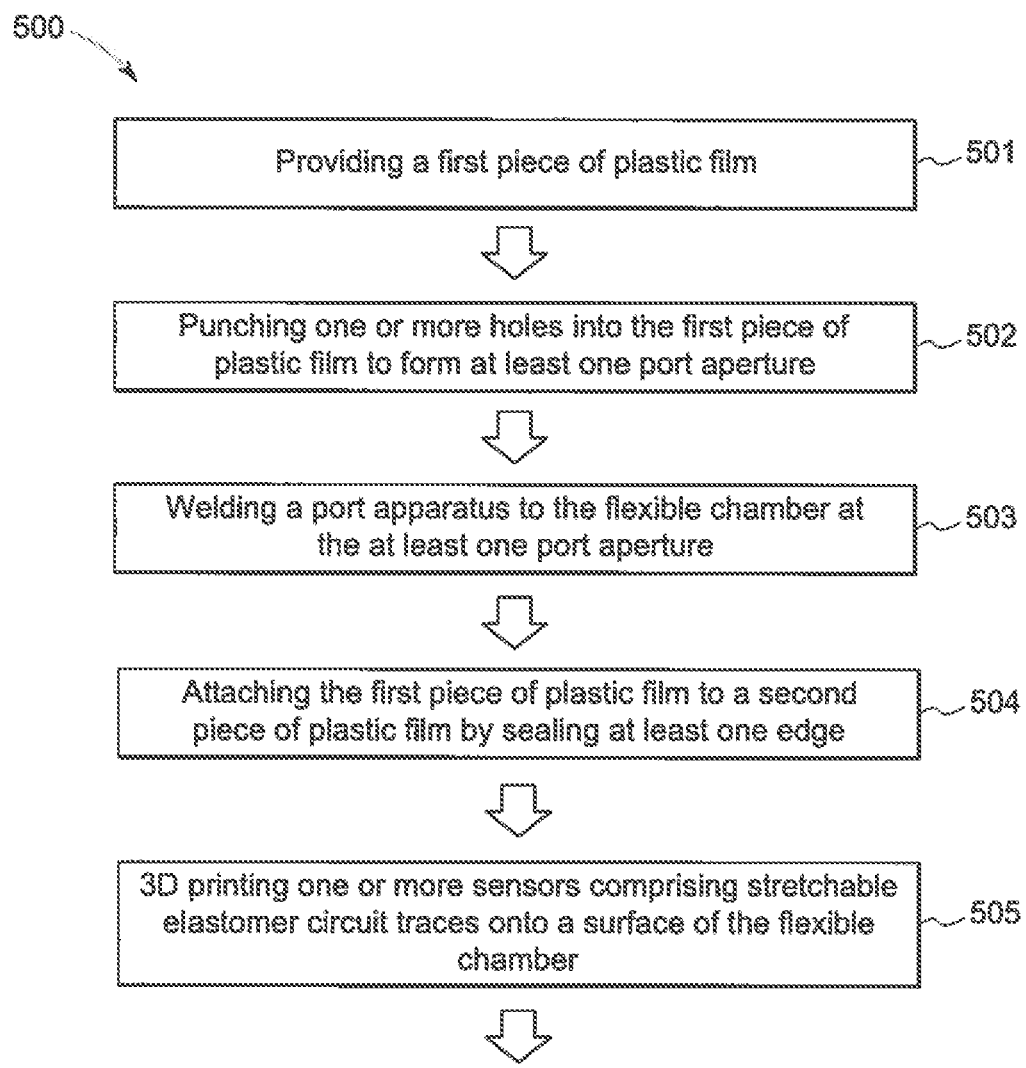
FIG. 5 shows a detailed schematic diagram on how to manufacture the flexible container with at least one sensor as described herein.

FIG. 5 shows a schematic diagram of an embodiment of a method 500 of manufacturing the flexible container described herein with the at least one sensor affixed thereto to form, for example, a cell bag bioreactor. The method generally commences at step 501 where a first piece of plastic film 501 is provided. The plastic film is typically made of a polyethylene copolymer, but could be made from any of a number of polymers, including but not limited to polypropylene, polycarbonate, or polypropylene.

At step 502, one or more holes are punched or otherwise formed at predetermined locations, depending on the desired configuration, into the first piece of plastic film to form the at least one port aperture for receiving a corresponding port body or assembly. At step 503, the port body or assembly is affixed welded by heat seal to the first piece of plastic film at the at least one port aperture. At step 504, the first piece of the plastic film is attached to a second piece of plastic film by sealing at least one edge formed at least one interface between the first and second pieces of plastic film, to form a closed or sealed flexible volume or chamber. And at step 505, one or more sensors including at least one strain sensor comprising a deformable electrical conducting element are printed via a 3D printing method onto a surface of the flexible chamber at one or more predetermined configurations.

It should be noted that the above-described steps need not be performed in the recited order. For example, step 505 wherein one or more sensors including at least one strain sensor comprising a deformable electrical conducting element are printed via a 3D printing method onto a surface of the flexible chamber at one or more predetermined configurations may be performed prior to step 502 wherein one or more holes are punched at predetermined locations into the first piece of plastic film to form the at least one port aperture. Hence, the order of steps shall not be construed in a limiting sense.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. In the embodiments described above, the term fluid shall mean a liquid, a gas, a plasma, a flowing material or substance, or any combination thereof. In some such embodiments, said fluid, in whatever form, comprises a cell culture comprising one or more types of living or active cells, viruses, prions, self-replicating molecules, or any combination thereof, in a culture media which may include one or more inert substances and/or supporting materials to encourage growth and proliferation such as, for example, oxygen and nutrients.

What is claimed is:

1. A system for monitoring viscosity changes of a fluid stored in a volume, the system comprising:
    a flexible chamber defining the volume to receive and hold the fluid;
    a motion generator to induce a wave motion within the fluid;
    at least one sensor, affixed at least in part to a portion of the flexible chamber, which measures at least a strain on a portion of the flexible chamber and generates an associated strain output, the strain output effectuated by the wave motion of the fluid within the flexible chamber, wherein the strain output correlates to a viscosity value of the fluid; and
    a computer or controller which receives the strain output from the sensor at a given time compares the viscosity value associated with the strain output to a reference viscosity value, and determines, based on the comparison, whether to adjust the wave motion generated by the motion generator.

2. The system of claim 1, wherein the fluid comprises cell culture media.

3. The system of claim 1, wherein the flexible chamber is a cell bag bioreactor.

4. The system of claim 3, wherein the flexible chamber is a cell bag bioreactor comprising at least one port.

5. The system of claim 4, wherein the at least one sensor is 3D printed directly onto the cell bag bioreactor.

6. The system of claim 1, wherein the at least one sensor comprises 3D printed stretchable conductive elastomers.

7. The system of claim 1, wherein the fluid comprises a cell culture and the viscosity of the fluid is affected by changes in cell proliferation within the cell culture.

8. The system of claim 1, wherein the motion generator is a rocking platform.

9. The system of claim 7, wherein the rocking platform adjusts the wave motion by altering at least one of angle, speed, and acceleration of the platform.

10. A method for monitoring viscosity changes of a fluid stored in a flexible chamber defining a volume, the method comprising:
    generating a wave motion in the fluid which imparts a strain on a surface of the flexible chamber;
    receiving a strain output from at least one sensor, said strain output corresponding to the strain on the surface of the flexible chamber at a given time;
    comparing a viscosity value associated with the strain output to a reference viscosity value; and
    determining, based on the comparison, whether to adjust the wave motion of the fluid in the flexible chamber or maintain the current wave motion of the fluid in the flexible chamber.

11. The method of claim 10, wherein the at least one sensor is affixed at least in part to a portion of the flexible chamber, measures at least a strain on a portion of the flexible chamber, and generates the strain output, the strain output effectuated by the wave motion of the fluid within the flexible chamber.

12. The method of claim 11, wherein the fluid comprises a cell culture with or without supporting cell culture media, wherein an increase in viscosity correlates to an increase in the volume of the cell culture within the fluid.

13. The method of claim 10, wherein the flexible chamber is a cell bag bioreactor.

14. The method of claim 10, wherein the fluid comprises a cell culture with or without supporting cell culture media and the viscosity of the fluid is affected by changes in cell proliferation within the cell culture.

15. The method of claim 11, wherein the at least one sensor is 3D printed directly onto the cell bag bioreactor.

16. The method of claim 10, wherein the at least one sensor comprises 3D printed stretchable conductive elastomers.

17. The method of claim 10, wherein the motion generator is a rocking platform.

18. The method of claim 17, wherein the rocking platform adjusts the wave motion by altering at least one of angle, speed, and acceleration.

19. A method for manufacturing the flexible chamber of claim 1, the method comprising:
   providing a first piece of plastic film;
   forming one or more holes into the first piece of plastic film to form at least one port aperture;
   affixing a port apparatus to the flexible chamber at the at least one port aperture;
   attaching the first piece of plastic film to a second piece of plastic film by sealing at least one edge; and
   3D printing one or more sensors comprising stretchable elastomer circuit traces onto a surface of the flexible chamber.

20. The method of claim 19, wherein the flexible chamber is a cell bag bioreactor.

\* \* \* \* \*